(12) United States Patent
Patois et al.

(10) Patent No.: US 6,204,379 B1
(45) Date of Patent: *Mar. 20, 2001

(54) PREPARATION OF CAPROLACTAM

(75) Inventors: Carl Patois, Riedisheim; Michel Spagnol, Lyons, both of (FR)

(73) Assignee: Rhodia Fiber & Resin Intermediates, Courbevoie Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,875

(22) PCT Filed: Oct. 3, 1997

(86) PCT No.: PCT/FR97/01761

§ 371 Date: Jul. 27, 1999

§ 102(e) Date: Jul. 27, 1999

(87) PCT Pub. No.: WO98/15529

PCT Pub. Date: Apr. 16, 1998

(30) Foreign Application Priority Data

Oct. 4, 1996 (FR) .................................................. 96/12326

(51) Int. Cl.$^7$ .................................................. C07D 201/08
(52) U.S. Cl. .................................................. 540/538
(58) Field of Search ............................................. 540/538

(56) References Cited

U.S. PATENT DOCUMENTS 4,636,576 * 1/1987 Bhattacharva et al. ............... 558/277
5,616,773 * 4/1997 Stahl et al. ............................ 558/353

FOREIGN PATENT DOCUMENTS 0 729 944   9/1996  (EP) .
97/02228    1/1997  (WO) .

* cited by examiner

Primary Examiner—Bruck Kifle
(74) Attorney, Agent, or Firm—Burns, Doane, Swecker & Mathis, L.L.P.

(57) ABSTRACT

The present invention concerns the aminomethylation of pentenoic acid derivatives, by reaction with carbon monoxide, hydrogen and ammonia, for preparing caprolactam. More precisely, it is directed to a method for preparing caprolactam wherein the aminomethylation of pentenoic acid derivatives is carried out by reaction with carbon monoxide, hydrogen, and ammonia, at a temperature higher than 30° C. and in the presence of a catalyst with a base of at least one metal of Group VIII of the Periodic Table.

19 Claims, No Drawings

PREPARATION OF CAPROLACTAM

The present invention relates to the aminomethylation of pentenoic acid derivatives, by reaction with carbon monoxide, hydrogen and ammonia, in order to prepare caprolactam.

Caprolactam is the constituent of Nylon 6.

Numerous access routes to caprolactam exist, in particular from butadiene.

In particular, the successive preparation of a pentenenitrile by hydrocyanation of butadiene and then of a 5-cyanovaleric acid derivative, the carbonyl functional group being introduced by virtue of a carbonylation reaction or a hydroformylation reaction, and finally the conversion of the nitrile functional group to an amine functional group by a hydrogenation reaction, in order to obtain caprolactam and/or aminocaproic acid, has been envisaged. This process suffers from a large number of stages and requires the successive use of hydrocyanic acid and then of carbon monoxide, which can be harmful to the economic advantage of such a process.

In the process of the invention, caprolactam is obtained directly in a single stage from a pentenoic acid derivative, which is much simpler than the processes already envisaged from butadiene.

The pentenoic acid derivatives are, for example, esters. Such esters can for their part be readily obtained from butadiene according to well-described processes.

The metals which can catalyse this type of reaction are, for example, cobalt, palladium, rhodium or iridium.

The reaction employed here, which consists in converting a C=C compound to a CH—CH—CH$_2$—N product, has the name of aminomethylation. The aminomethylation of olefins is a known reaction catalysed by a variety of metals from group VIII; however, it is generally limited to the synthesis of secondary or tertiary amines, because the amine formed by aminomethylation is a better nucleophile than the starting amine. Thus, in the case of the use of ammonia, the product formed by aminomethylation of the olefin with ammonia reacts faster with another olefin than ammonia.

We have found that this limitation could be circumvented by using the intramolecular cyclization of the amine to a lactam. By way of example, this aim is achieved by using a pentenoic acid ester as substrate.

More specifically, the invention consists of a process for the preparation of caprolactam, characterized in that the aminomethylation of pentenoic acid derivatives is carried out, by reaction with carbon monoxide, hydrogen and ammonia, at a temperature greater than 30° C. and in the presence of a catalyst based on at least one metal from group VIII of the Periodic Classification of the Elements.

The pentenoic acids to which the invention relates are the various isomers of this compound, namely cis-pent-2-enoic, trans-pent-2-enoic, cis-pent-3-enoic, trans-pent-3-enoic and pent-4-enoic acids.

The derivatives of the pentenoic acids in the context of the invention are the compounds where the OH group of the acidic functional group has been replaced by a group, such as O—R or S—R, in which R represents an alkyl, cycloalkyl, aralkyl, aryl or silyl residue. More particularly, the derivatives used are the esters of alcohols comprising from 1 to 6 carbon atoms.

Use may be made of any mixture of derivatives of the various pentenoic isomers. However, use will preferably be made of mixtures where the derivatives of the pent-3-enoic acids predominate. The mixture of pentenoic acid derivatives can additionally comprise a minor amount of 4-methylbutyrolactone and of derivatives of other carboxylic acids comprising 5 carbon atoms, such as valeric acid, at a content preferably of less than 20% by weight and more preferably still of less than 10% by weight.

The concentration by weight of the pentenoic acid derivatives can vary within wide limits, depending on whether the reaction is carried out in the presence of a solvent or not and depending on the degree of progression of the reaction. By way of indication, it is, for example, between 5 and 99% by weight.

The reaction is advantageously carried out in the presence of a solvent. The amount of solvent employed varies between 10 and 95% by weight of the reaction mixture.

This solvent can be highly varied in nature. The choice may in particular be made of alcohols, aliphatic ethers, aromatic ethers, mixed ethers, nitrites, acyclic amides, cyclic amides, aliphatic hydrocarbons, aromatic hydrocarbons, chlorinated aliphatic hydrocarbons, chlorinated cycloaliphatic hydrocarbons or the mixtures of several of these solvents.

In the case where an alcohol is used as solvent or as part of a mixture of solvents and where the aminomethylation of a pentenoic acid ester is being carried out, the alcohol corresponding to the said ester is preferably used.

As non-limiting examples, the solvents which can be used are ethanol, methanol, isopropanol, diphenyl ether, isopropyl ether, acetonitrile, dimethylformamide, N-methylpyrrolidone, benzene, toluene, xylenes, chlorobenzenes, dichloromethane, dichloroethanes, hexane and cycloh-xane.

In the context of an industrial implementation of the process, recycling operations carried out on the catalyst and on the unreacted pentenoic acid derivatives can result in the introduction into the reaction mixture of more or less significant amounts of other compounds and in particular of caprolactam product. In the context of the invention, these compounds will be regarded as forming an integral part of the solvent system.

The catalyst is based on at least one metal from group VIII. Use may be made, as source of such catalysts, of the metallic elements or various organometallic complexes or salts, such as chlorides, iodides, bromides, metal carbonyls, or carboxylates, these being mentioned as non-limiting examples.

The catalyst is preferably based on at least one of the metals taken from rhodium, iridium, ruthenium, iron or cobalt. The catalyst is optionally used in combination with promoters, such as phosphorus derivatives and/or $Q^{n+}X_n$ salts, where n represents 1 or 2, Q representing an alkali metal element (n=1) or an alkaline earth metal element (n=2) and X a halogen.

Preferably, Q is chosen from lithium, sodium, potassium, magnesium and calcium and X is chosen from fluorine, chlorine, bromine and iodine.

The phosphorus derivatives are of the $R^1R^2R^3P$ type, where $R^1$, $R^2$ and $R^3$ are the same or different and represent an alkyl or aralkyl or cycloalkyl residue comprising from 1 to 20 carbon atoms which can additionally comprise one or more atoms taken from nitrogen, oxygen, sulphur, phosphorus and iron and which can form one or more rings with one another. The following are suitable as non-limiting illustrative examples of such promoters: triphenylphosphine, tricyclohexylphosphine, phosphanorbornadienes, phosphanorbornenes, phosphanorbornanes, 1,2-bis(diphenylphosphino)ethane, 1,2-bis(diphenyl-phosphinomethyl)cyclobutane, 1,3-bis(diphenyl-phosphino)

propane, 1,4-bis(diphenylphosphino)butane or 1,1'-bis(diphenylphosphino)ferrocene.

The amount of catalyst to be employed can vary within wide limits. In general, an amount, expressed as total number of moles of metals used as catalysts per litre of reaction mixture, of between $10^{-5}$ and $10^{-1}$ leads to satisfactory results. Lower amounts can be used but it is observed, however, that the reaction rate is low. Higher amounts are only disadvantageous from an economic viewpoint. This amount is preferably between $10^{-4}$ and $5\times10^{-2}$ mol per liter of reaction mixture.

The aminomethylation reaction can be carried out at a temperature generally between 60° C. and 230° C. and preferably between 80° C. and 200° C.

The carbon monoxide partial pressure, measured at 25° C., is between 0.5 and 300 bar. It is preferably between 2 and 200 bar and more preferably still between 5 and 150 bar.

The hydrogen partial pressure, measured at 25° C., is between 0.5 and 200 bar. It is preferably between 1 and 150 bar and more preferably still between 2 and 100 bar.

The hydrogen/carbon monoxide molar ratio is between 10/1 and 1/10, preferably between 5/1 and 1/2.

The amount of ammonia involved can vary within wide limits. However, it is preferable to use an excess with respect to the substrate. The ammonia/substrate molar ratio is between 1/1 and 100/1 and preferably between 1.1/1 and 50/1.

The process of the invention can be implemented continuously or batchwise. There will therefore be grounds for adjusting the various operating conditions defined above according to the implementation chosen.

The example which follows illustrates the invention.

88.6 mg of $Rh_6(CO)_{16}$, 1.11 g of methyl pentenoate and 20 ml of methanol are successively introduced into a 125 ml Hastelloy® B2 autoclave; the autoclave is closed and 4.58 g of $NH_3$ are introduced via an isolation chamber. The autoclave is then pressurized with 40 bar of CO and 80 bar of hydrogen at 20° C. Agitation by shaking is begun and the temperature of the autoclave is brought to 150° C.; the total pressure is then 163 bar. After 195 min, the pressure in the autoclave has decreased by 2 bar; heating is then halted. After cooling, the autoclave is degassed and then opened; the khaki-green reaction mass is analysed by Gas Chromatography (GC). The caprolactam yield of 33% is confirmed by coupled GC/MS (mass spectrometry).

What is claimed is:

1. Process for the preparation of caprolactam, which comprises reacting pentenoic acids or compounds thereof where the OH group of the pentenoic acids has been replaced by O—R or S—R where R represents an alkyl, cycloalkyl, aralkyl, aryl, or silyl with carbon monoxide, hydrogen and ammonia, in a single stage at a temperature greater than 30° C. and in the presence of a catalyst based on at least one metal from group VIII of the Periodic Classification of the Elements.

2. Process according to claim 1, wherein the reaction is carried out in the presence of a solvent.

3. Process according to claim 1, wherein the total amount of catalyst is between $10^{-5}$ and $10^{-1}$ mol per liter of reaction mixture.

4. Process according to claim 1, wherein the temperature is between 60° C. and 230° C.

5. Process according to claim 1, wherein the catalyst is based on at least one of the metals taken from rhodium, iridium, ruthenium, iron or cobalt.

6. Process according to claim 1, wherein the ammonia/substrate molar ratio is between 1/1 and 100/1.

7. Process according to claim 1, wherein the carbon monoxide partial pressure, measured at 25° C., is between 0.5 and 300 bar.

8. Process according to claim 1, wherein the hydrogen partial pressure, measured at 25° C., is between 0.5 and 200 bar.

9. Process according to claim 1, wherein the hydrogen/carbon monoxide molar ratio is between 10/1 and 1/10.

10. Process according to claim 1, wherein said compounds are an ester.

11. The process according to claim 1, wherein the total amount of catalyst is between $10^{-4}$ and $5\times10^{-2}$ mol per liter of reaction mixture.

12. The process according to claim 4, wherein the temperature is between 80° C. and 200° C.

13. The process according to claim 6, wherein the ammonia/substrate molar ratio is between 1.1/1 and 50/1.

14. The process according to claim 7, wherein the carbon monoxide partial pressure measured at 25° C., is between 2 and 200 bar.

15. The process according to claim 14, wherein the carbon monoxide partial pressure, measured at 25° C., is between 5 and 150 bar.

16. The process according to claim 8, wherein the hydrogen partial pressure is between 2 and 150 bar.

17. The process according to claim 16, wherein the hydrogen partial pressure is between 5 and 100 bar.

18. The process according to claim 9, wherein the hydrogen/carbon monoxide molar ratio is between 5/1 and 1/2.

19. The process according to claim 10, wherein the ester is a methyl ester or an ethyl ester.

\* \* \* \* \*